(12) United States Patent
Koley et al.

(10) Patent No.: US 10,191,004 B2
(45) Date of Patent: Jan. 29, 2019

(54) MICROCANTILEVER BASED SELECTIVE VOLATILE ORGANIC COMPOUND (VOC) SENSORS AND METHODS

(71) Applicant: University of South Carolina, Columbia, SC (US)

(72) Inventors: Goutam Koley, Anderson, SC (US); Ifat Jahangir, West Columbia, SC (US)

(73) Assignee: University of South Carolina, Columbia, SC (US)

( * ) Notice: Subject to any disclaimer, the term of this patent is extended or adjusted under 35 U.S.C. 154(b) by 269 days.

(21) Appl. No.: 14/887,448

(22) Filed: Oct. 20, 2015

(65) Prior Publication Data
US 2016/0109395 A1    Apr. 21, 2016

Related U.S. Application Data

(60) Provisional application No. 62/122,447, filed on Oct. 21, 2014.

(51) Int. Cl.
G01N 27/12    (2006.01)

(52) U.S. Cl.
CPC ......... G01N 27/128 (2013.01); G01N 27/125 (2013.01)

(58) Field of Classification Search
CPC .............................. G01N 27/04; G01N 27/128
See application file for complete search history.

(56) References Cited

U.S. PATENT DOCUMENTS

| | | | |
|---|---|---|---|
| 8,236,569 B2 | 8/2012 | Vogt et al. | |
| 8,252,598 B2 | 8/2012 | Koley et al. | |
| 8,580,099 B2 | 11/2013 | Koley | |
| 8,762,075 B2* | 6/2014 | Loui | G01N 25/18 702/24 |
| 2009/0112071 A1* | 4/2009 | LeBoeuf | A61B 5/02116 600/301 |
| 2012/0293271 A1* | 11/2012 | Nayfeh | H03B 5/1228 331/108 R |
| 2014/0166483 A1* | 6/2014 | Chow | B03C 5/005 204/451 |

OTHER PUBLICATIONS

Guo et al.; "Risk Assessment of exposure to volatile organic compounds in different indoor environments," *Environ. Res.*; (2004) 94(1), pp. 57-66.

Singh, et al.; "Evidence from the Pacific troposphere for large global sources of oxygenated organic compounds," *Nature* (2001) 410 (6832), pp. 1078-1081.

(Continued)

*Primary Examiner* — Jermele M Hollington
*Assistant Examiner* — Feba Pothen
(74) *Attorney, Agent, or Firm* — Dority & Manning, P.A.

(57) ABSTRACT

Microcantilevers and systems incorporating the microcantilevers are described that can be utilized to perform selective detection of VOCs. The systems can detect VOCs at temperatures below the auto-ignition temperature of the VOCs and the microcantilevers need not be functionalized with any reactive groups particularly designed for the VOCs to be detected. The microcantilevers are triangular microcantilevers that can be formed of high bandgap semiconductors such as AlGaN/GaN heterojunction semiconductors.

23 Claims, 9 Drawing Sheets

(56) References Cited

OTHER PUBLICATIONS

Gall; "The Si-Planar-pellistor array, a detection unit for combustible gases," *Sens. Actuators B* (1993) 16(1), pp. 260-264.

Ke, et al.; "A MEMS-based Benzene Gas Sensor with a Self-heating $WO_3$ Sensing Layer," *Sensors* (2009) 9, pp. 2895-2906.

Qazi, et al.; "III-V Nitride based piezoresistive microcantilever for sensing applications," *Appl. Phys. Lett.*(2011) 99, pp. 193508.

Qazi, et al.; "$NO_2$ Detection Using Microcantilever Based Potentiometry," *Sensors* (2008) 8, pp. 7144.

Qazi, et al.; "Trace gas detection using nanostructured graphite layers," *Appl. Phys. Lett.* (2007) 91, pp. 233101.

Tang, et al.; "Detection of Femtomolar Concentrations of HF Using an $SiO_2$ Microcantilever," *Anal. Chem.* (2004) 76; pp. 2478-2481.

Koley, et al.; "Gas sensing using electrostatic force potentiometry," *Appl. Phys. Lett.* (2007) 90, pp, 173105.

Koley, et al.; "Investigation of Cantilever Resonance Applied to Potentiometric Sensing," *MRS Proceedings* (2006) 951, [6 pages].

Canetta, et al.; "Sub-picowatt resolution calorietry with a bi-material microcantilever sensor," *Appl. Phys. Lett.* (2013) 102, pp. 103112.

Liu. J.O., et al.; "Heated atomic force microscope cantilever with high resistivity for improved temperature sensitivity," *Actuators A* (2013) 201, pp. 141-147.

Lee, et al.; "Thermal conduction from microcantilever heaters in partial vacuum," *J. Appl. Phys.* (2007) 101(1), pp. 014906-014906.

Lee, et al.; "Microcantilever hotplates: Design, fabrication, and characterization," *Sens. Actuators A* (2007) 136, pp. 291-298.

Lee, et al.; "Electrical, Thermal, and Mechanical Characterization of Silicon Microcantilever Heaters," *J. Microelectromech. Syst.* (2006) 15(6), pp. 1644.

Pinnaduwage, et al.; "Sensitive detection of plastic explosives with self-assembled monolayer-coated microcantilevers," *Appl. Phys. Lett.* (2003) 83 (7), pp. 1471-1473.

Loui, et al.; "Detection and discrimination of pure gases and binary mixtures using a dual-modality microcantilever sensor," *Sens. Actuators A* (2010) 159(1), pp. 58-63.

Tetin, et al.; "Modeling and performance of uncoated microcantilever-based chemical sensors," *Sens. Actuators B* (2010) 143(2), pp. 555-560.

Brown, et al.; "Concentrations of Volatile Organic Compounds in indoor Air—A Review," *Indoor Air* (1994) 4(2), pp. 123-134.

Neuberger, et al.; "High-Electron-Mobility AlGaN/GaN Transistors (HEMTs) for Fluid Monitoring Applications," *Phys. Status Solidi A* (2001) 185(1), pp. 85-89.

Talukdar, et al.; "High frequency dynamic bending response of piezoresistive GaN microcantilevers," *Appl. Phys. Lett.* (2012) 101, pp. 252102.

Davies, et al.; "Fabrication of GaN cantilevers on silicon substrates for microelectromechanical devices," *Appl. Phys. Lett.* (2004) 84(14), pp. 2566-2568.

\* cited by examiner

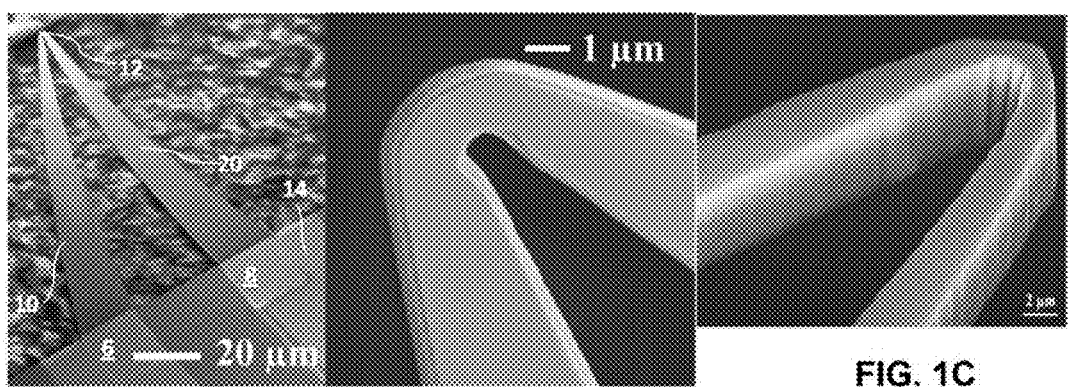
FIG. 1A  FIG. 1B  FIG. 1C
FIG. 1
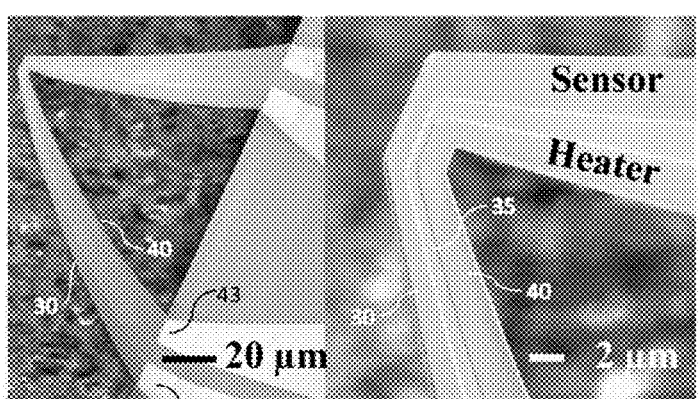
FIG. 1D  FIG. 1E
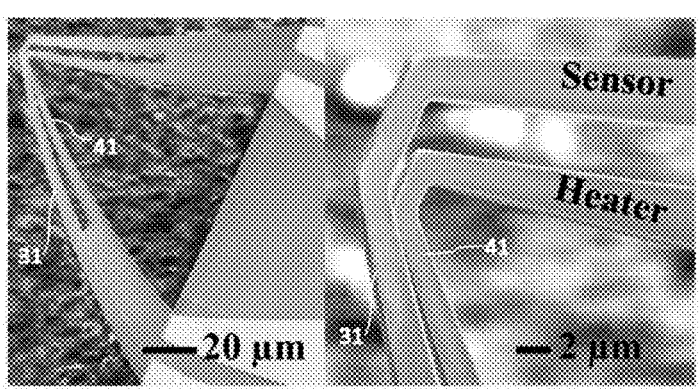
FIG. 1F  FIG. 1G

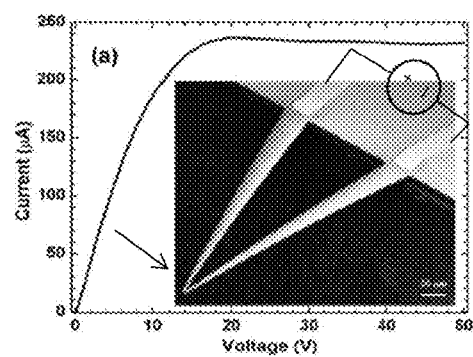 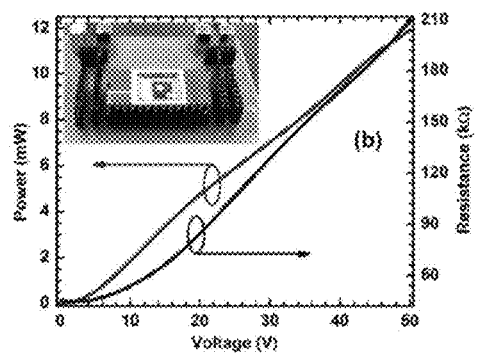
FIG. 2A  FIG. 2B
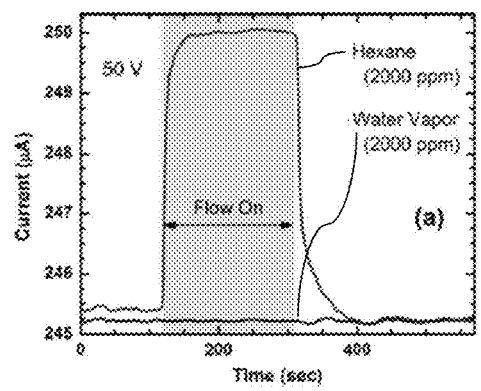 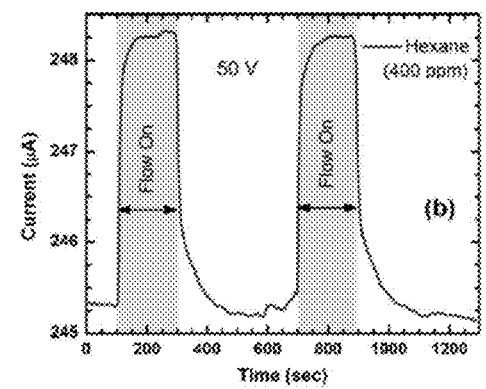
FIG. 3A  FIG. 3B

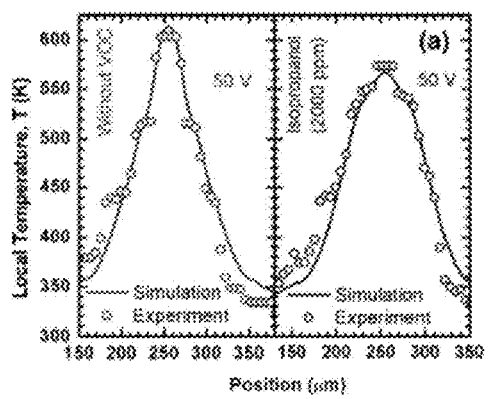
FIG. 5A
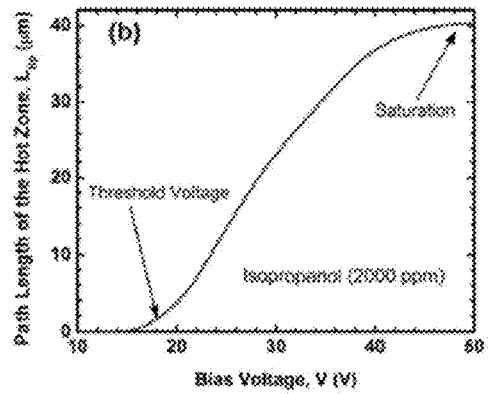
FIG. 5B
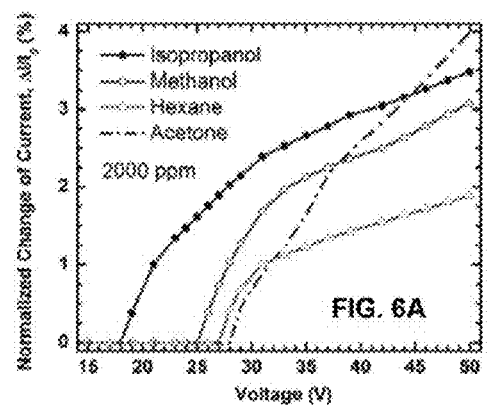
FIG. 6A
FIG. 6B
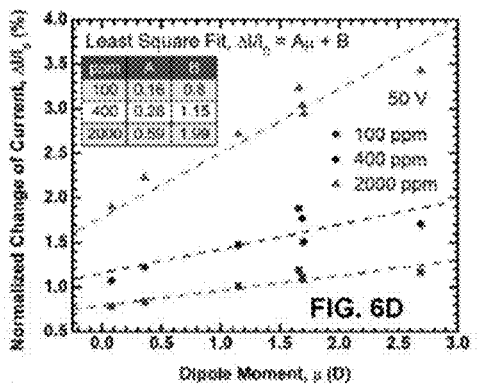
FIG. 6D
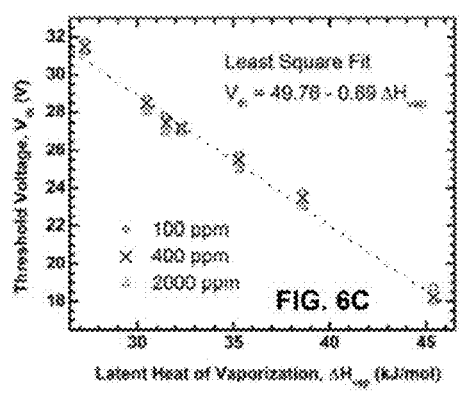
FIG. 6C

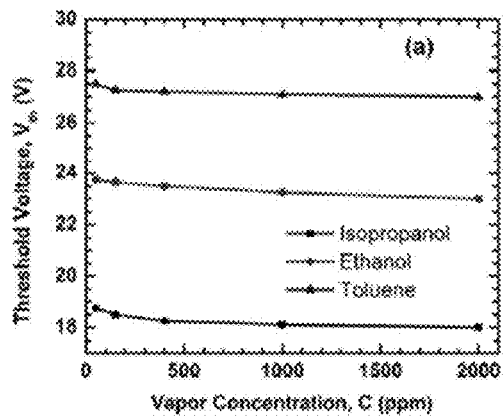
FIG. 7A
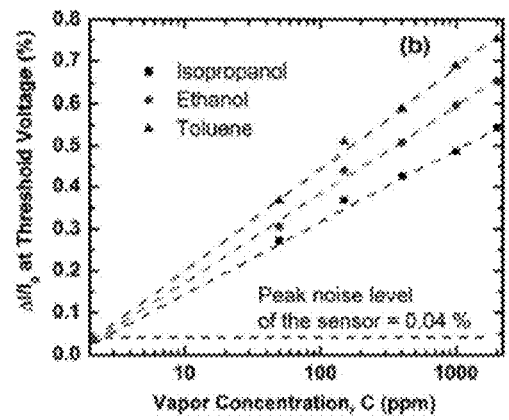
FIG. 7B
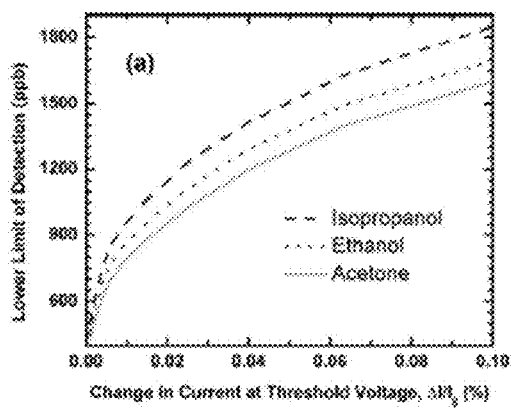
FIG. 8A
(b) Theoretical Detection Limit of Analytes for 0.001% Change in Current at Threshold Voltage
| Analyte | Detection Limit (ppb) |
|---|---|
| Isopropanol | 502.42 |
| Ethanol | 465.31 |
| Methanol | 455.93 |
| Toluene | 448.51 |
| Hexane | 441.65 |
| Acetone | 432.72 |
| Diethyl Ether | 408.33 |
FIG. 8B

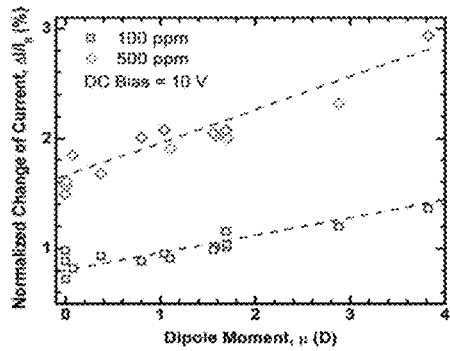
FIG. 11A
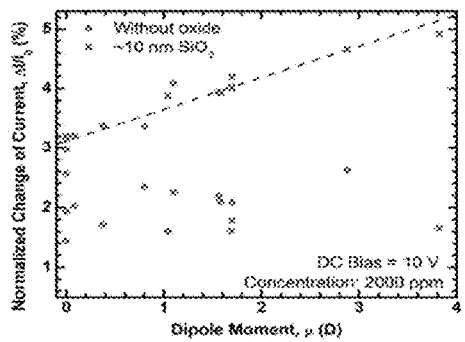
FIG. 11B
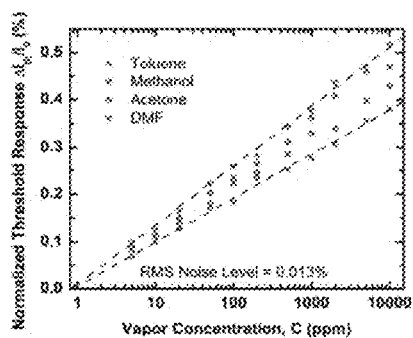
FIG. 12A
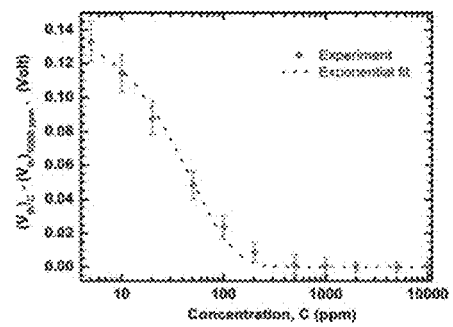
FIG. 12B
FIG. 13A
FIG. 13B
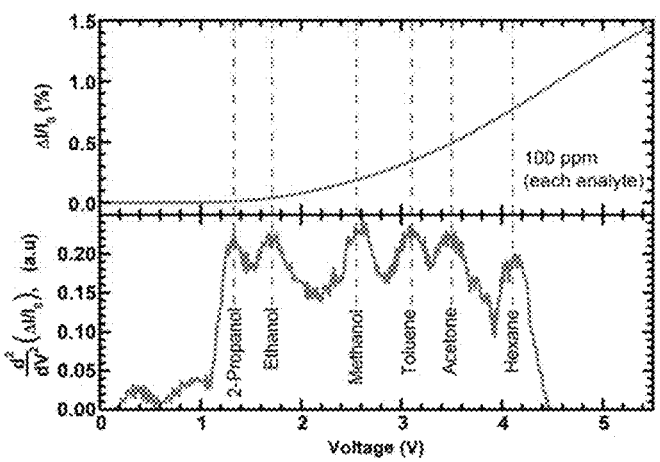

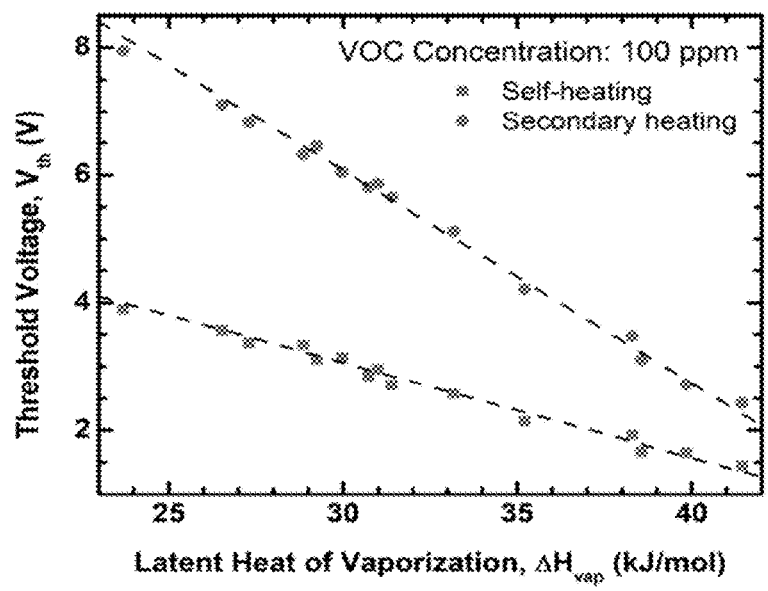
FIG. 14
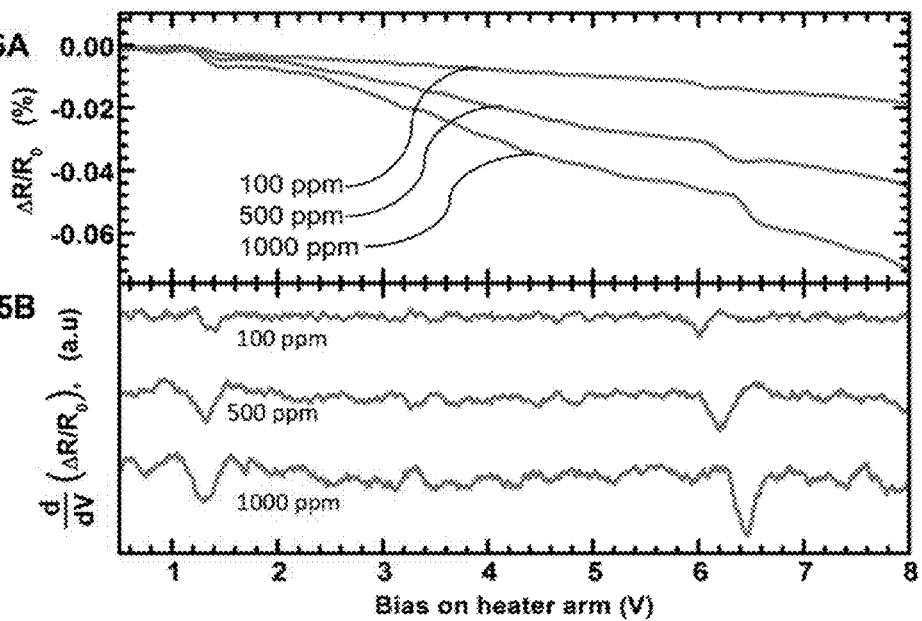

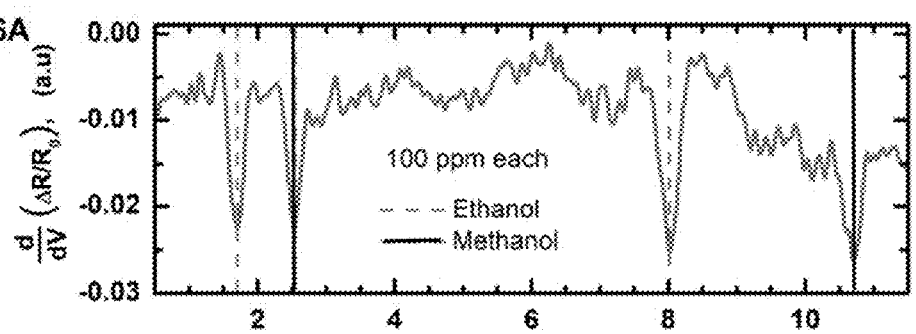
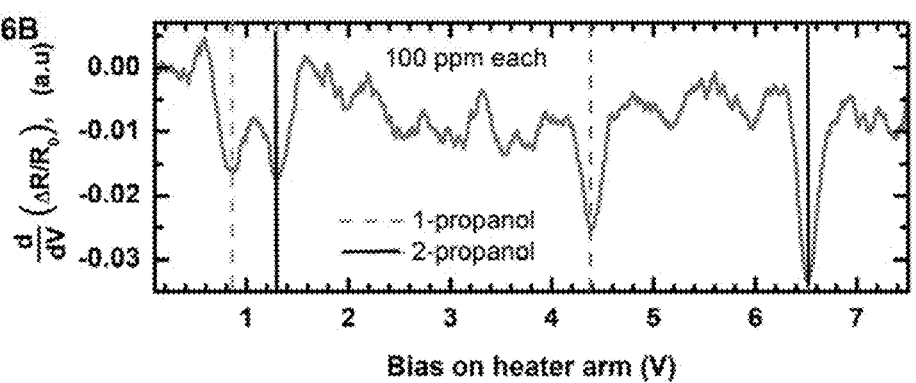

MICROCANTILEVER BASED SELECTIVE VOLATILE ORGANIC COMPOUND (VOC) SENSORS AND METHODS

CROSS REFERENCE TO RELATED APPLICATION

This application claims filing benefit of U.S. Provisional Patent Application Ser. No. 62/122,447 having a filing date of Oct. 21, 2014, which is incorporated herein by reference in its entirety.

GOVERNMENT SUPPORT CLAUSE

This invention was made with government support under grant nos. ECCS-0846898, IIP-1343437, and ECCS-1341866 awarded by the National Science Foundation. The government has certain rights in the invention.

BACKGROUND

Detection of volatile organic compounds (VOCs), which are widely used in industrial processes and household products, is very important due to significant health hazards associated with these materials. VOCs are commonly detected using photo-ionization detectors (PIDs), suspended hot bead pellistors or heated metal oxide semiconductors having functionalized layers. The detection methodology using PIDs is based on high-energy (typically >10.5 eV) photon induced ion generation, while that using hot bead pellistors takes advantage of the exothermic reaction (from auto-ignition of the VOCs) to produce a change in resistance. Heated metal oxide based sensing (e.g., $TiO_2$ or $SnO_2$) also relies upon a change in resistance, but at a temperature below the auto-ignition temperature of the VOCs.

Unfortunately, these techniques suffer from the problem of high power requirement as well as poor selectivity among VOCs, which is often important for proper identification of the source of a problem. Although the heated metal oxide method requires somewhat lower operational power, it involves complicated metal oxide functionalization processes.

Microcantilevers offer excellent opportunities for molecular sensing that arise out of their high sensitivity to various physical parameter changes induced by the analyte molecules. Microcantilever heaters, which are extremely sensitive to changes in thermal parameters, have been widely utilized for calorimetry, thermal nanotopography, and thermal conductivity measurements. Due to the small area of the microcantilever that needs to be heated (e.g., the tip of a triangular microcantilever), they also offer the possibility of reduced power consumption for high temperature operation. However, achieving repeatable and reliable functionalization of a microcantilever, especially over a small area, is a challenge that has thwarted practical applications of microcantilever-based sensors. On the other hand, unfunctionalized microcantilevers (typically made of silicon) are not particularly sensitive toward specific analytes, and are generally accepted to be incapable of performing selective detection. Thus, only a handful of studies utilizing uncoated microcantilevers to perform unique molecular detection have been reported. In these studies, detection has generally been based on changes in physical properties of the media surrounding the cantilever (i.e. viscosity, thermal conductivity, or changes in the analyte (i.e. deflagration temperature). Unfortunately, previous techniques are applicable only to a few specific analytes, and selective detection still remains a major challenge, especially when the analytes are diluted, are present in minute quantities or have similar physical properties as is the case for VOCs.

What are needed in the art are systems and methods that can quickly and efficiently identify different VOC's.

SUMMARY

According to one embodiment, disclosed is a system for identifying a VOC. For instance, a system can include a fluid flow path for carrying a VOC and can also include a microcantilever in the flow path. The microcantilever can be a triangular microcantilever and can include two arms that extend from a base and a tip at the junction of the two arms. The microcantilever can also be in electrical communication with a power source such that a driving voltage can be applied across the microcantilever. Sections of the microcantilever arm can exhibit a temperature dependent resistance and the microcantilever can be designed (e.g., through geometric design, materials of construction, field induced conductivity variation, etc) such that upon contact of the heated microcantilever with a VOC and under the driving voltage, the electrical resistance of the tip can vary from that of the arms.

Also disclosed are methods for using a VOC identification system. For instance, a method can include flowing a gas/vapor containing one or more VOCs to contact the microcantilever described above. The method also includes applying a voltage bias across the microcantilever and thereby heating the microcantilever to a temperature at which a condensed VOC in contact with or near the microcantilever can vaporize. One or more electrical characteristics of the microcantilever (e.g., the current and/or the overall resistance) can then be monitored as the voltage bias across the microcantilever is varied, and a threshold voltage can be identified that is indicative of a VOC contained in the stream. The threshold voltage is a voltage at which the rate of change of the electrical characteristic of the microcantilever exhibits a sudden change and is related to the latent heat of vaporization ($\Delta H_{vap}$) of the VOC(s) in contact with the microcantilever.

The microcantilever can include a single channel or multiple channels that are independently in electrical communication with a power supply. For instance, in one embodiment, the microcantilever can include a heating channel through which the voltage bias is varied during a sensing protocol and also can include a sensing channel that can be held at a fixed voltage bias. In this embodiment, the sensor channel can be monitored to examine the change in one or more electrical characteristics of the sensor channel as a result of the secondary heating provided via the heater channel. This can provide additional information regarding the VOC (or VOCs) contained in the stream.

According to one embodiment, the method can also include determining the magnitude of a current change when the microcantilever is contacted with one or more VOCs at or above the threshold voltage, which can provide additional information regarding the VOC (or multiple VOCs).

BRIEF DESCRIPTION OF THE FIGURES

The present disclosure may be better understood with reference to the following figures, in which:

FIG. 1 presents several embodiments of microcantilever sensors as disclosed herein include single channel sensors (FIG. 1A, FIG. 1B, FIG. 1C), monolithic tip dual channel sensors (FIG. 1D, FIG. 1E), and split tip dual channel sensors (FIG. 1F, FIG. 1G).

FIG. 2A presents the current/voltage (I-V) characteristics of a V-shaped microcantilever sensor. The inset shows an SEM image of the microcantilever.

FIG. 2B presents the change of power and resistance with bias voltage for the cantilever of FIG. 2A. A photograph of a wire-bonded device mounted on a dual inline package (DIP) is shown in the inset.

FIG. 3A illustrates the response of a device to 2000 ppm of hexane and to water vapor at 50 V dc bias.

FIG. 3B illustrates the response of the device to 400 ppm of hexane in two consecutive cycles to demonstrate the repeatability of the sensor behavior.

FIG. 5A presents simulated and experimentally determined temperature profiles for a heated cantilever in intrinsic condition and in the presence of 2000 ppm of isopropanol vapor at 50 V bias.

FIG. 5B illustrates the electrical path length of the heated tip resistance (denoted by $R_{tip}$), $L_{tip}$, as a function of bias voltage for 2000 ppm of isopropanol vapor.

FIG. 6A presents composite plots of normalized change in current (%) with change in voltage for isopropanol, methanol, acetone and hexane at 2000 ppm molar concentration; showing a distinct voltage for each analyte below which there is no change in current.

FIG. 6B presents the dipole moment (μ) and latent heat of evaporation ($\Delta H_{vap}$) for different volatile organic compounds (VOCs).

FIG. 6C presents the linear relation between the threshold voltage of sensing ($V_{th}$) and the latent heat of evaporation ($\Delta H_{vap}$) for different VOCs at molar concentrations of 100, 400 and 2000 ppm.

FIG. 6D presents the correlation between normalized change in current (%) at 50 V and dipole moment (μ) for VOCs at 100, 400 and 2000 ppm molar concentrations. Least square fit parameters for the fitted straight lines are given in the table in the inset.

FIG. 7A illustrates the dependence of $V_{th}$ on concentration of isopropanol, ethanol and toluene.

FIG. 7B illustrates the dependence of change in current at threshold voltage on concentration of isopropanol, ethanol and toluene.

FIG. 8A presents the theoretical lowest concentration of isopropanol, ethanol and acetone that can be detected for a given change in current at threshold voltage by use of the disclosed methods.

FIG. 8B is a compilation of theoretical lower limits for various analytes at 0.001% change in current at threshold voltage.

FIG. 11A presents the correlation between normalized change in current (%) at 10 V DC bias and dipole moment (p) for multiple VOCs at 100 and 500 ppm molar concentrations.

FIG. 11B illustrates the relationship between normalized change in current and dipole moment obtained for several different VOCs at 2000 ppm concentration for a bare microcantilever and a microcantilever coated with $SiO_2$.

FIG. 12A presents the normalized threshold response, defined by the normalized change in current within a 20 mV voltage range around $V_{th}$, shown as a function of concentration for four analytes.

FIG. 12B presents the experimental shift of $V_{th}$ with concentration variation along with exponential fit.

FIG. 13A illustrates the normalized change in current (%) obtained from a Angle channel microcantilever heater in presence of six analytes (100 ppm of each)—2-propanol, ethanol, methanol, toluene, acetone and hexane.

FIG. 13B is the second derivative of the curve shown in FIG. 13A with respect to the applied bias (V).

FIG. 14 illustrates the linear relationship between threshold voltage of sensing ($V_{th}$) and latent heat of evaporation ($\Delta H_{vap}$) for different VOCs at 100 ppm molar concentration obtained from each channel of a monolithic tip dual channel microcantilever heater.

FIG. 15A illustrates the normalized change in resistance (%) for 100, 500 and 1000 ppm of 2-propanol, as measured on the sensor channel using a spilt tip dual channel microcantilever heater (sensor channel biased at fixed 100 mV DC).

FIG. 15B provides the first derivative of each response curve shown in FIG. 15A, with respect to V.

FIG. 16A illustrates the first derivative of the normalized change in resistance (%) for 100 ppm (each) of ethanol and methanol as measured on the sensor channel using a spilt tip dual channel microcantilever heater.

FIG. 16B illustrates the first derivative of normalized change in resistance (%) for 100 ppm (each) of 1-propanol and 2-propanol as measured on the sensor channel using a split tip dual channel microcantilever heater.

DETAILED DESCRIPTION

Figure 4A:
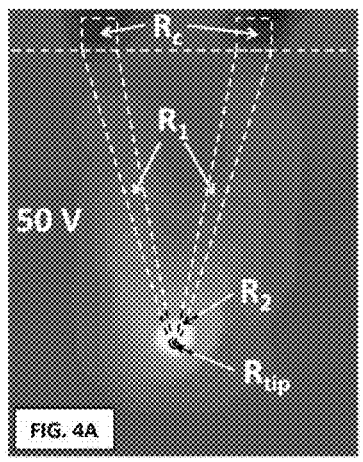
FIG. 4A is an infrared image of the cantilever shown in FIG. 2A at 50 V bias.

The following description and other modifications and variations to the present disclosure may be practiced by those of ordinary skill in the art, without departing from the spirit and scope of the present disclosure. In addition, it should be understood that aspects of the various embodiments may be interchanged both in whole and in part. Furthermore, those of ordinary skill in the art will appreciate that the following description is by way of example only, and is not intended to limit the disclosure.

Chemical elements may be discussed in the present disclosure using theft common chemical abbreviation, such as commonly found on a periodic table of elements. For example, hydrogen is represented by its common chemical abbreviation H; helium is represented by its common chemical abbreviation He; and so forth.

As used herein, the prefix "nano" refers to the nanometer scale (e.g., from about 1 nm to about 1,000 nm) and the prefix "micro" refers to the micrometer scale (e.g., from about 1,000 nm (i.e., 1 µm) to about 1 millimeter).

In general, disclosed herein are microcantilevers and systems incorporating the microcantilevers that can be utilized to perform selective detection of VOCs. VOCs as may be detected by use of the system can include, without limitation, alcohols, ethers, ketones, alkanes and aromatic compounds. Beneficially, the systems can detect VOCs at temperatures below the auto-ignition temperature of the VOCs and the microcantilevers need not be functionalized with any reactive groups particularly designed for the VOCs to be detected. As utilized herein, the term "volatile organic compound (VOC)" generally refers to organic chemicals that have a high vapor pressure at ordinary room temperature. Their high vapor pressure results from a low boiling point, which causes large numbers of molecules to evaporate or sublimate from the liquid or solid form of the compound and enter the surrounding air at relatively low temperatures.

Basically, a detection process can include monitoring the electrical characteristics (e.g., the current and/or the overall resistance) of a heated microcantilever held under a driving voltage bias while in the presence of one or more VOCs. The microcantilever is designed to exhibit temperature dependent differential resistance variation across the microcantilever, i.e., the resistance can vary to a greater extent in one section of the microcantilever as compared to other sections as the voltage bias is increase while the microcantilever is contacted with the VOC. During a sensing protocol, a voltage bias applied to the microcantilever can be varied over time as the electrical characteristics are monitored for sudden changes. The electrical characteristics can change under the variable voltage bias due to differential heating and related changes in resistance of the different sections of the microcantilever. For example a voltage bias of from 0 V to about 100 V, or from 0 V to about 50 V can be swept over the microcantilever. According to the detection process, the rate of current (or overall resistance) change of the microcantilever as the driving voltage is varied can exhibit a sudden alteration at a threshold voltage, and this threshold voltage has been found to be distinct for different VOCs. In particular, this distinct threshold voltage has been found to correlate with the latent heat of vaporization for the organic analytes in contact with the microcantilever. Thus, by determination of the threshold voltage at which the rate of change of the current (or overall resistance) of the microcantilever under a varying applied voltage suddenly alters, the VOC can be identified.

As utilized herein the term "threshold voltage ($V_{th}$)" generally refers to the lowest applied voltage at which current magnitude change through a microcantilever varies by 0.05% or more within an applied voltage range of 0.1 V. The mid-value of that 0.1V voltage range is then defined as $V_{th}$. This definition assumes a noise level of about 0.013% and a signal to noise ratio of about 2.5 or more in presence of an analyte. In a low noise environment, the threshold voltage can be lower, which would be easily identifiable for one of skill in the art based upon this definition.

Additional information regarding VOCs can be obtained by use of the system. For instance, in one embodiment, the system can include a polar material in the microcantilever. In this embodiment, the magnitude of the current change through the microcantilever upon being placed in contact with a VOC can provide information with regard to the identity of the VOC. Upon contacting a heated microcantilever with a VOC while under an applied voltage, the current can show a dramatic change. The magnitude of this current change can vary depending upon the particular analyte(s) in contact with the microcantilever. In fact, the magnitude of the current through the microcantilever has been found to be related to the molecular dipole moment of the VOC and is believed to be due to polarization effects in the polar microcantilever material(s) brought about by contact with a polar VOC.

Modification in microcantilever geometry can likewise be utilized to provide additional information with regard to one or more VOCs placed in contact with the microcantilever. For instance, in one embodiment, a microcantilever can include multiple different channels, e.g., one or more heating channels and one or more separate sensing channels. During a sensing protocol, the different channels can be operated under different parameters. For example, one channel can be driven under a static voltage and another channel can be driven under a varying voltage. Moreover, the different channels can be formed with a monolithic construction (i.e., of a single piece) or separated with an air gap between the channels. As discussed further herein, examination of the electrical characteristics of the different channels of the system can provide additional information about VOCs placed in contact with the microcantilever By use of the disclosed systems, VOCs at concentrations as low as about 5 parts per million (ppm) can be detected selectively with a noise limited resolution of about 5 ppm or less in some embodiments.

The detection systems include a microcantilever that can exhibit a temperature dependent differential in resistance at different sections across the length of the microcantilever arm. The differential temperature and hence resistance across the length of the microcantilever arm can be brought about through variation in shape of the microcantilever from end to end, variation in materials across the microcantilever, variation in induced conductivity across the microcantilever, etc. as well as through combinations of such features. By way of example, differential in resistance along length of the cantilever can be brought about by changing the width and/or thickness of the cantilever, by selectively doping certain regions of the cantilever and/or by using a separate metal contact on top or bottom face of the cantilever to modulate the carrier concentration with an applied electric field. In the latest case, part of the cantilever can act like a field effect transistor, and an electric field can modulate the carrier concentration and conductivity in the channel.

In one embodiment, the microcantilever can be a V-shaped triangular microcantilever including two arms that extend from a base to meet at a narrowed point at a distance from the base, one embodiment of which is illustrated in FIG. 1A. The tips of two triangular microcantilevers are illustrated in FIG. 1B and FIG. 1C. In this embodiment, the temperature differential can be obtained primarily through the variation in microcantilever arm shape, as the extremely narrow tip area will exhibit a greater change in temperature (and thus resistance) during a sensing protocol as compared to the wider end sections of the microcantilever.

As shown in FIG. 1A, a triangular microcantilever can include a first arm 10 and a second arm 20 extending respectively from a base 14. Each arm 10, 12 can be in electrical communication with a first metal contact 6 and a second metal contact 8, respectively, as shown. The first arm 10 extents from the base 14 for a first length, and the second arm 20 extents from the base 14 for a second length. The first arm and the second arm are connected together at a tip 12 to form the v-shaped microcantilever. The first arm 10 and the second arm 20 can be the same or different lengths as one another. For instance, the first and second arms 10, 20 can independently be about 50 micrometers or more in length, for instance from about 100 micrometers to about 1 millimeter, or from about 150 micrometers to about 500 micrometers in some embodiment. The distance between the arms at the base can generally be from about 20 micrometers or more, for instance from about 50 to about 300 micrometers, or from about 100 micrometers to about 200 micrometers in some embodiments. The thickness of the microcantilever arms can vary, depending upon the materials of the arms and the methods of formation, but can generally be about 50 micrometers or less, for instance from about 0.5 micrometer to about 20 micrometers, in some embodiments.

In this embodiment, the cross sectional area of the arms are tapered from the base 14 to the tip 12. The cross sectional area of the tip can be quite small and as such can be highly resistive to current flow as compared to the wider areas at either end of the cantilever arm. For instance, the arms 10, 20 can have a width of from about 5 to about 30 micrometers at either end where they meet the base 14 and can taper to a width of from about 0.5 micrometers to about 5 micrometers where they meet at the tip. While the illustrated embodiments have a regular taper from the base 14 to the tip 12, it should be understood that microcantilever arms that decrease in cross sectional area across a length of the arm can do so in any fashion, e.g., step-wise, in a regular or irregular taper, etc. For instance, in one embodiment the microcantilever arms can taper in one dimension (e.g., thickness) and remain constant in a second dimension (e.g., width) along the length. In another embodiment, the microcantilever arms can taper in all cross-sectional dimensions. In addition, it should be understood that the cross sectional shape of a microcantilever arm can have any shape, e.g., square, rectangular, circular, regular or irregular polyhedron, etc. Such variations can be utilized to design particular electrical characteristics of the microcantilever according to known practice.

The materials used to form the microcantilever can be any material in which a driving voltage can be used to generate a current across/through the length of the microcantilever as described. In general, the microcantilever can include one or more semiconductors, which can provide the capability to tune the temperature dependent differential in resistance among sections of the microcantilever through variation in geometry and/or the materials of formation. By way of example, differential doping of the materials of construction along the length of the microcantilever arms can be utilized to control temperature dependent resistance differential in the microcantilever.

In one embodiment, a microcantilever can include a wide bandgap semiconductor, i.e., a semiconductor that exhibits a band gap of about 3 eV or greater. Examples of wide bandgap semiconductors for use in forming a microcantilever can include, without limitation, wide bandgap Group IV and Group V semiconductor elements and Group III-V, Group II-V and Group II-VI semiconductor compounds. In one particular embodiment, a microcantilever can include a wide bandgap semiconductor obtained by combining one or more group III elements (e.g., Al, Ga, In) with one or more group V elements (e.g., N, P, As, Sb). Examples of Group III-V semiconductors as may be incorporated in a microcantilever can include GaAs, MP, InN, GaP and GaN. In one embodiment a wide bandgap material of a microcantilever can include $In_{1-y}Al_yAs$, $In_{1-y}Al_yP$, $Al_{1-y}Ga_yAs$ and $In_{1-y}Ga_yP$ with y varying from 0 to 1. A wide bandgap material of a microcantilever can be doped or semi-insulating as is generally known in the art.

A microcantilever can incorporate multiple materials in a composite arrangement. For instance, a microcantilever can incorporate multiple semiconductor materials, e.g., multiple wide bandgap semiconductor materials, in a composite structure. In one embodiment, a microcantilever can be formed from multiple semiconductor materials in a stacked arrangement to provide a homojunction and/or a heterojunction in the device. As utilized herein, a "heterojunction" generally refers to an interface that occurs between two layers or regions of dissimilar crystalline semiconductors that have unequal band gaps. A "homojunction" in contrast, generally refers to an interface between two layers or regions of dissimilar crystalline semiconductors with essentially equal bandgaps. For example, a microcantilever can include a stacked arrangement of semiconductor materials that exhibit a heterojunction at each interface.

In one particular embodiment, the microcantilever can include a Group III-V, e.g., a Group III-N, heterojunction based composite material such as an AlGaN/GaN based composite material. For instance, an entire triangular microcantilever can be formed of a Group III-N heterojunction based composite material. AlGaN/GaN based composite materials can offer a unique opportunity for realizing the microscale sensors, taking advantage of the presence of high carrier (electron) density in close proximity to the surface, which can facilitate highly efficient surface heating. In addition, strong spontaneous polarization of III-Nitride surfaces can allow the microcantilever to interact well with VOCs, which are typically strongly polar in nature. Group III-N heterojunction based microcantilevers are also capable of operating at high temperature and in harsh environments due to the chemical inertness and wide bandgap of III-Nitrides. Due to the commercial availability of high quality III-Nitride heterojunction epilayers on Si substrates, the fabrication of the microcantilever sensors can also be quite straightforward according to known fabrication techniques.

FIG. 1D and FIG. 1E illustrate another embodiment of a microcantilever in which the triangular microcantilever includes two different channels 30, 40. Each channel is in electrical communication with a separate set of contacts, as shown. In particular channel 30 is in electrical communication with contact 33 and channel 40 is in electrical communication with contact 43. Thus, the driving voltage for a current through each channel can be independently operated. For example, the first channel 30 can be driven with a static voltage and can be utilized as a sensor channel as illustrated in FIG. 1E, and the second channel 40 can be driven with a variable driving voltage including a sweeping voltage bias and can be utilized as a heater channel as illustrated in FIG. 1E. Any driving force variation between the two is encompassed herein, however, including different static driving voltages, different variable voltages, etc. In addition, a microcantilever can include additional channels, and is not limited to only a single channel construction as is FIG. 1A-FIG. 1C or two channels as in FIG. 1D-FIG. 1G.

In the embodiment of FIG. 1D and FIG. 1E, the microcantilever is of a monolithic construction, in which the channels are components of a single piece construction and include a solid dielectric or insulator material as an current flow barrier 35 between the two. For instance, the channels 30, 40 can be formed of one or more wide bandgap semiconductor materials (e.g., AlGaN/GaN heterojunction material) and the barrier 35 between the two can be a dielectric (e.g., a semi-insulating GaN material without the AlGaN layer).

In another embodiment, a multi-channel microcantilever arm can be of a split channel construction, as illustrated in FIG. 1F and FIG. 1G. In this embodiment, the two channels 31, 41 can be as described above such that their electrical parameters can be independently controlled, but the channels 31, 41 can be separated by an air gap along all or a portion of the channels. Of course, a multi-channel cantilever can include both monolithic channels and split channels, as desired.

During use, the channels of a multi-channel cantilever can be controlled independently to provide information about VOCs placed in contact with the microcantilever. For instance, one of the channels (e.g., 40, 41) can be operated in a self-heating mode, in which a variable voltage bias can be applied to the channel and varying electrical characteristics (e.g., current) through the channel can be monitored, similarly to a single channel microcantilever heater as illustrated in FIG. 1A, FIG. 1B, and FIG. 1C. The second channel, 30, 31, can be operated in a secondary heating mode, in which the channel is biased at a fixed DC bias (e.g., 100 mV) and electrical characteristics can be monitored as the voltage bias through the associated channel (40, 41) is swept. This channel will also exhibit a change in current and overall resistance; however, the changes in this channel (30, 31) will be as a result of secondary heating caused by the associated heater channel.

When monitoring the electrical characteristics of a dual channeled microcantilever as illustrated in FIG. 1F and FIG. 1G, examination of the change in electrical characteristics of the sensing channel 31 with change in the temperature across the sensing channel 31 can provide information regarding the VOC in contact with the microcantilever. For instance, (and as described in more detail in the Examples section below) examination of the resistance change across the sensing channel 31 can demonstrate a first large rate change variation due to the change of the temperature profile on the heater channel 41 (i.e., a faster increase in temperature of the heater channel due to sudden resistance change of the channel 41 at the threshold voltage of this channel), which can be captured by examination of the characteristics of the sensor arm 31 as a sudden but relatively small change in rate of change of resistance in the sensor arm 31 (at about 1.3 V on FIG. 15B). As the voltage bias is further increased on the heater channel 41, the temperature on the sensor channel 31 will also continue to increase. At a point, the sensor channel will demonstrate a sudden change in rate of change of resistance when the sensor channel reaches the voltage threshold in that channel, which generates a second peak on the graph of FIG. 15B at about 6.4V.

As can be seen in FIG. 15B, higher concentration of analyte in the system tends to demonstrate a higher threshold voltage in the sensor channel. At higher analyte concentration, the heat transfer rate between the two channels can decrease due to the lower thermal conductivity of the analyte. Thus, a higher bias is needed to reach the temperature at which the sudden change occurs, which causes the second peak to shift to a higher threshold voltage. As this threshold voltage shift between the directly heated channel and the indirectly heated sensing channel is dependent upon the thermal conductivity of the VOC examined, this shift can provide further information with regard to the identity of a VOC in contact with the microcantilever.

While the threshold voltage between directly heated and indirectly heated channels of a multi-channel device can vary greatly, as illustrated in FIG. 15B, in general, the threshold voltage of any one channel of a device has little dependence on analyte concentration. For instance, the threshold voltage value of a single channel device can vary by about 0.15 volt or less over a VOC concentration reduction of from about 2000 ppm to about 5 ppm. This indicates that the threshold voltage of a VOC remains effectively constant over a large variance in concentration, and thus can be used to reliably identify VOCs over their significant detection range, particularly for indoor environments.

Without wishing to be bound to any particular theory, a resistive circuit model is provided to explain the observations between threshold voltage for detection and latent heat of vaporization for a microcantilever sensor as encompassed herein. The model is based upon a triangular shaped single channel microcantilever sensor formed of a heterojunction AlGaN/GaN composite material, one embodiment of which is illustrated in FIG. 1A. While the below discussion is directed to this material, for which temperature and resistance are positively correlated (i.e., an increase in temperature leads to an increase in resistance), it should be understood that the disclosed sensors are not limited to materials exhibiting this relationship. In particular, materials for which temperature and resistance are negatively correlated (e.g., an increase in temperature leads to a decrease in resistance) are also encompassed herein, and the models are understood to be equally applicable, but with the opposite correlations of the thermal and electrical characteristics.

Heat transfer and Joule heating simulations were performed using finite difference methods to compute the thermal characteristics of a microcantilever sensor, which were in good agreement with the experimental observations as detailed in the Experimental section, below. A noise limited resolution of 5 ppm for various analytes has been established experimentally with an ideal detection limit below 1 ppm for low noise environments being predicted from the simulation results.

To facilitate the model description, it was assumed that the overall cantilever resistance of a single channel microcantilever sensor consists of several lumped resistors connected in series, each describing the resistance of a specific section along the arms of the cantilever. These resistances are shown in FIG. 4A as $R_c$ (contact resistance), $R_1$ (side arm resistance), $R_2$ (resistance near the tip) and $R_{tip}$ (resistance of the tip region). A circuit diagram of the model is provided in the inset of FIG. 4C.

As determined experimentally, at lower biases (<10 V), a device exhibits a current/voltage relationship (I-V) with almost constant resistance (FIG. 2A), indicating the absence of any significant self-heating. At higher biases (>10 V), power ($I^2R$) loss increases, causing the tip temperature and resistance $R_{tip}$ to go up. However, due to the relative sizes of the different cantilever sections, as the bias voltage increases, the temperatures at other sections of the device including the contacts and the side arms do not increase as much as at the tip area, and the differential temperature increase across the microcantilever causes a differential resistance variation across the microcantilever, i.e., the resistance in these sections do not increase to the extent that the resistance increases at the tip section.

When a volatile vapor is injected into a chamber containing the microcantilever sensor, the vapor molecules can initially tend to condense in close proximity of the cantilever, but the increased heat at the tip region will immediately cause them to evaporate. In addition there will be more evaporation per unit area of cantilever in the tip region than in the other, lower temperature sections of the microcantilever. This results in a relatively large loss of thermal energy from this tip region causing its temperature to become lower and thereby leading to a decrease in the related resistance $R_{tip}$. The sections of the microcantilever away from the tip are at a lower temperature and do not participate in rapid evaporation of analyte molecules to the extent that it is carried out at the tip, and as such the thermal energy loss due to the evaporation of VOCs is not significant in these sections and the related resistances $R_2$ and $R_1$ will likewise demonstrate little change. Since the whole device is under a constant voltage bias, reduction in $R_{tip}$, will cause an increase in voltage drop across $R_1$ and $R_2$ ($R_c$, is likely to be much smaller and the voltage drop across it can be neglected). Since $R_2$ can be expected to be larger than $R_1$ at higher temperature, the voltage drop across $R_2$ can be more significant, resulting in a higher temperature rise in the $R_2$ region as compared to the $R_1$ region and consequently larger increase in resistance. Therefore, the total resistance between the arms of the microcantilever is affected by the opposite changes in $R_{tip}$ and $R_2$, in agreement with the IR image line scan shown in FIG. 4C under isopropanol flow. Throughout this disclosure, the term "isopropanol" is intended to be interchangeable and synonymous with the term "2-propanol."

At a moderate bias voltage, e.g. about 10 V, even though a VOC vapor can cause a reduction in $R_{tip}$ (by reducing temperature at the tip through evaporation), the increase in $R_2$ (due to increase in temperature) can compensate for it, since the overall rise in temperature is still low at that bias. Thus the rate of current change can remain unchanged even in presence of a VOC vapor at lower biases. However, as the bias voltage is increased for a given VOC flow, and depending on the extent of the temperature and $R_{tip}$ drop of the tip region (which correlates with the molar latent heat of evaporation, $\Delta H_{vap}$ of the VOC), a threshold voltage ($V_{th}$) bias can be reached where the magnitude of the reduction in $R_{tip}$, would be greater than the magnitude of the increase in $R_2$. Thus a sudden variation in the rate of change of the current through the microcantilever can be observed as the voltage continues to increase above the threshold voltage. As the temperature of the microcantilever tip can depend upon the latent heat of vaporization of the VOC that is being vaporized by the thermal energy of the tip, the threshold voltage can likewise be dependent upon the latent heat of vaporization. Existence of a unique threshold voltage for different materials, and its dependence on $\Delta H_{vap}$, has been experimentally observed as described further below, and is shown in the figures (e.g., FIG. 6A).

A theoretical model based on heat transfer (considering conduction, convection and radiation) and Joule heating has also been developed. The model is normalized using a number of experimental observations so that the calculated temperature profiles at known conditions (i.e. bias, analyte composition and concentration) match well with the measured values. The calibrated model can be used to predict outputs at conditions for which experimental values are difficult to obtain; it can also lead to valuable information on other quantities such as local variation of resistivity and so on. The model can be a system of different equations which can be solved by various numerical techniques, such as finite difference method and finite element method to name a few.

By way of example and without limitation, one embodiment of a model can be based on known equations for heat transfer (Equation (1) and (3)) and Joule heating (Equation (2)) that can be solved simultaneously and iteratively using finite difference method (e.g., using MATLAB).

$$\rho_d C_p \frac{\partial T}{\partial t} + \nabla \cdot (K_c \nabla T + u\rho_d C_p T) + Q_{vap} = \frac{1}{\rho}|\nabla V|^2 \quad (1)$$

$$-\nabla \cdot d\left(\frac{1}{\rho(T)}\nabla V - Je\right) = 0 \quad (2)$$

$$n \cdot (K_c \nabla T) = q_0 + h(T_{inf} - T) + \varepsilon\sigma(T_{inf}^4 - T^4) \quad (3)$$

Equation (1) and (2) have been solved for different domains of the system, whereas Equation (3) was used as a boundary condition at the interface of the solid microcantilever and surrounding air domains. Here, $\rho_d$=material density,
Cp=heat capacity,
T=absolute temperature,
$K_c$=thermal conductivity,
$Q_{vap}$=heat loss due to evaporation of analyte molecules (when applicable),
$J_e$=electrical current density,
V=potential profile,
$\rho(T)$=electrical resistivity as a function of temperature,
n=unit vector normal to the interface,
h=temperature dependent coefficient of convection for air,
$T_{inf}$=temperature far away from the cantilever,
$\varepsilon$=emissivity of the solid surface,
$\sigma$=Stefan-Boltzmann constant.

The temperature dependence of the electrical resistivity can be modeled using least square polynomial fit of experimental data, which can be obtained by measuring the resistance of a sample device on a temperature-calibrated hot plate.

For an arbitrary surface area $A_h$, amount of heat loss $Q_{vap}$ per unit time at a given concentration C and partial pressure $P_p$ is given by $$Q_{vap} = \frac{1}{4} A_h P_p C \frac{\Delta H_{vap}}{N_A} \sqrt{\frac{3M}{kT}} \quad (4)$$

Here,
$\Delta H_{vap}$=the molar latent heat of evaporation,
$N_A$=Avogadro's number (6.02×10²³ molecules/mop,
M=molecular mass,
k=Boltzmann's constant (1.38×10⁻²³ JK⁻¹).

Using this embodiment of a model, calculated temperature profiles have been obtained and are shown in FIG. 5A in conjunction with experimentally determined temperature profiles. For simplicity, it has been assumed that heat was taken away by evaporation of the molecules only at the tip region.

As previously discussed, materials for use in forming the microcantilevers can include materials that exhibit strong polarization properties. As such, correlations between the magnitude of the molecular dipole moment of potential analyte VOCs and the magnitude of current change at an applied bias have also been explored. It has been found that as the dipole moment of the analyte increases, the response magnitude also increases, as shown in FIG. 6D. This is expected since the molecules with higher dipole moment are expected to have stronger interaction with a highly polar surface. This can cause a larger change in tip temperature and hence in the tip resistance and the overall magnitude of the current change. Although the physical mechanism of the molecular interaction is unclear, it is believed that a polar surface can better attract polar VOC molecules toward it, and can allow them to condense to a certain extent. This attraction can vary depending upon the dipole moment of the molecules. When the condensed molecules again evaporate, the latent heat taken away (and hence the resistance change and the current response magnitude) can also be proportional to the molecular dipole moment. For example, acetone, in spite of having a rather low $\Delta H_{vap}$, was shown to cause the largest change in current of examined analytes at 50 V, and its dipole moment is the highest among all the analytes studied.

The effect of polarization has been clearly observed only at relatively high bias voltages (e.g., about 45V or greater). At low bias voltages, e.g., closer to the $V_{th}$ for a particular analyte, the response is primarily controlled by the temperature distribution of the tip as discussed previously. Although the polarization effect is also believed to be present at lower voltage bias, it is insignificant compared to the other effects. At high bias voltages, effective surface area of the hot zone near the tip tends to saturate (though temperature still keeps increasing), allowing the surface polarization to play a dominant role in controlling the heat transfer to the analyte molecules, and consequently the device response. The power dissipation and the tip temperature continue to increase as the voltage bias goes up; however the device response has been found to be stable at about 50 V bias in spite of significant self-heating. In regular ambient environment, the devices were tested for up to 90 V bias repeatedly for several days and it was concluded that a 50 V bias could certainly be used for reliable and repeatable results. While a smaller bias (e.g., from about 18 V to about 32 V) can be used for detecting $V_{th}$, a larger voltage bias of 50 V can be utilized to observe the other modality of the sensor that is related to the dipole moment of the analytes.

In order to more definitively identify the threshold voltage, it can also be useful to observe the dependence of current magnitude change at or near the threshold voltage. In the post-threshold biasing region, more and more analyte molecules can interact with the heated cantilever tip as the effective area of the hot zone increases with bias voltage. Increased temperature also increases the convection flow, creating a low pressure region in the vicinity of the heated tip of the cantilever. This can cause faster circulation of analyte vapor around the cantilever tip resulting in more molecules to interact with the tip per unit time. Therefore, just above the threshold voltage, for the same analyte concentration, current is believed to be primarily governed by the effective area of the heated tip region as evident in FIG. 7A and FIG. 7B, where the analyte with the lowest threshold voltage (isopropanol) has the lowest threshold current (defined below) believed to be due to the smaller effective area of hot zone at that voltage. Extrapolating all the curves toward low concentration gives a noise limited resolution of below 5 ppm.

The threshold current can be calculated by first taking a voltage bias that is slightly e.g., about 0.1 V, above the threshold voltage. The change in current is then measured upon contact with an analyte. In order to better characterize the threshold voltage, it may also be useful to observe the dependence of current magnitude change at the threshold voltage. The threshold current response (i.e. normalized change in current) can then be defined by the following relationship:

$$\frac{\Delta I}{I_0} = \frac{(I_{vap} - I_0)|_{v_{th}+0.1} - (I_{vap} - I_0)|_{v_{th}}}{I_0|_{v_{th}+0.1} - I_0|_{v_{th}}} \quad (5)$$

Where $I_{vap}$ and $I_0$ are the currents measured with and without analyte vapor, respectively.

The disclosed sensors can also be quite sensitive. As utilized herein, the term "sensitivity" with regard to a sensor generally refers to the percent change in current for one decade change in analyte concentration; change in current is calculated at threshold voltage using Equation (5). This sensitivity is denoted by S herein, and can be calculated using the following expression:

$$S = \frac{\Delta I/I_0|_{C_2} - \Delta I/I_0|_{C_1}}{\log(C_2/C_1)} \quad (6)$$

where $C_2$ and $C_1$ are the concentrations ($C_2 > C_1$) over which the sensitivity is being determined. The microcantilever sensors can exhibit a sensitivity of about 1% or less, for instance about 0.5% or less in some embodiments.

The present disclosure may be better understood with reference to the examples, set forth below Example 1

Triangular cantilevers were fabricated using AlGaN/GaN heterostructure epitaxial layers grown on a 628 μm thick (111) Si substrate. An example of a cantilever used is shown in the inset of FIG. 2A. The microcantilevers were designed to have tapered arms to maximize the temperature rise at the tip under an applied bias. Briefly, the formation process utilized 1.4 cm by 1.4 cm diced pieces of AlGaN/GaN high electron mobility transistor (HEMT) epilayer grown on silicon (111) wafer. $Cl_2/BCl_3$ plasma was used to isolate the cantilever mesa, followed by another deeper etch to define the GaN outline. Ti/Al/Ti/Au metal stack was then deposited at the base using an electron beam evaporator followed by rapid thermal annealing to make good ohmic contact. The Si at the bottom of the pocket was etched from the backside of the sample using Bosch process, using PECVD $SiO_2$ as a hard mask. The total thickness of the cantilever was 2.3 μm; base width of each arm of the cantilever was 25 μm, which reduced to 3 μm at the tip. The arms were 100 μm apart at the base of the cantilever.

The experimental setup used for sensing VOCs involved a test chamber fitted with an inlet and an outlet. Two mass flow controllers were used to control the composition of the VOC produced by passing ultra-high purity (UHP) $N_2$ through a bubbler at room temperature, which was diluted with UHP $N_2$. The outlet of the chamber was connected to a dry pump to quickly remove the analyte from the test chamber. For the sensing experiments, dilute analyte vapors were flown into the test chamber (arrow, FIG. 2A) for a fixed duration under a constant DC bias applied to the device (FIG. 2A). The electrical and sensing characterizations were performed using an Agilent B2902 source measuring unit. The wire-bonded device mounted on a 28-pin dual inline package (DIP) is shown in the inset of FIG. 2B.

The current/voltage (I-V) characteristics of the cantilevers thus formed are shown in FIG. 2A where a linear (low bias) and a saturation region (high bias) can be clearly identified. As shown in FIG. 2A, current rate of change was generally observed to decrease at higher biases (>20 V) as tip resistance increased rapidly with rise in temperature (because of the significant self-heating of the device). FIG. 2B shows the change in power and resistance with increasing bias, with >300% change in resistance (from 50 kΩ to 200 kΩ) as the bias changed from 0 to 50 V and a power dissipation of 12 mW at 50 V.

The device response upon exposure to 2000 ppm molar concentration of hexane vapor is shown in FIG. 3A, where the current changed from 245.8 µA to 250.2 µA (1.84% change) in about 30 s, at a device bias of 50 V. The rise time, defined by the time taken by the current to go from 10% to 90% of the steady state value, was found to be about 14 s (FIG. 3A). The fall time (defined as the time for the maximum signal to decay from 90% to 10% of its value) was found to be about 20 s. Comparable rise and fall times were observed for other analytes as well. For comparison, the response to 2000 ppm molar concentration of water vapor is also shown in FIG. 3A for a bias of 50 V. Since no response was observed, it confirmed the lack of interference from water vapor.

In FIG. 3B, the response of the device to 400 ppm of hexane vapor is shown for two consecutive cycles to demonstrate complete recovery and repeatability of the device. For each phase of exposure, a current change of 1.1% was observed with an increased rise time (20-30 s) and fall time (~35 s), which is expected at lower concentration.

The same device was used repeatedly for the same analyte and for different analytes over several months; no hysteresis or drift was observed at any occasion. The variation in sensor response was observed to be within ±2% of its average value for multiple instances of sensing performed for over a year, showing excellent accuracy and repeatability. Although the I-V characteristics of various devices in the same batch had slight variation (<5%), the normalized response (e.g. percentage change in current) was found to be very uniform for all sample devices, with an average deviation of ±3% or less for the response of different devices under various bias/sensing conditions.

FIG. 4A-FIG. 4D illustrate the temperature profile along the length of the cantilever. The images were obtained by use of infrared thermal microscopy and Raman spectroscopy. The outline of the cantilever is super-imposed on the thermal image of FIG. 4A. Lumped resistors $R_c$, $R_1$, $R_2$ and $R_{tip}$ represent different regions of the device and were used to model it as discussed above. The tapered shape of the cantilever gave rise to a sharp temperature variation along the arms, especially near the tip, as observed from the infrared (IR) image of the cantilever recorded using a temperature calibrated Inframetrics PM280 Ultra Cam fitted with IR microscopic lenses from Sierra Pacific Innovations Corporation. The microcantilever was a two-terminal self-heating device with the conducting channel serving as the heater. The entire V-shape of the cantilever acted as the heater-resistor. Temperature change in the microcantilever, especially near the tip region was found to control the change in resistance between the two ohmic contacts at the base.

Figure 4B:
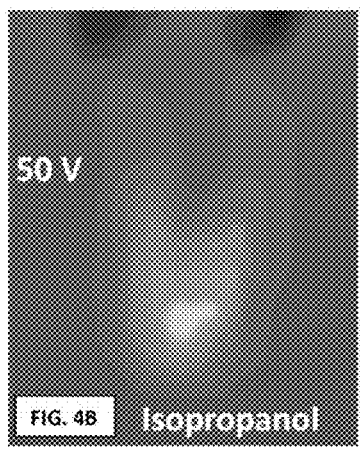
FIG. 4B is an infrared image of the cantilever shown in FIG. 2A at the same bias, but in the presence of isopropanol (i.e., 2-propanol) vapor with a molar concentration of 2000 ppm.
Figure 4C:
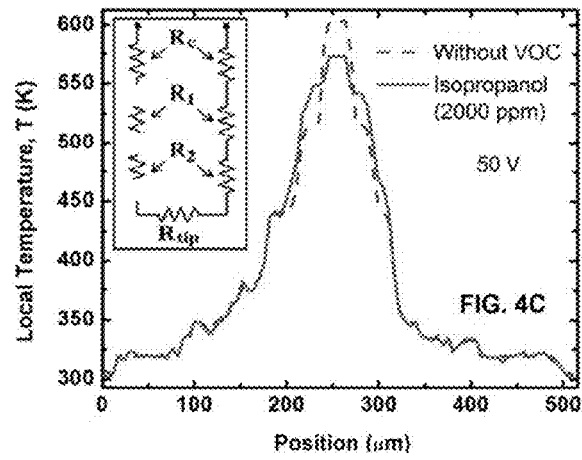
FIG. 4C is a line scan of temperature along the cantilever as shown in FIG. 4A and FIG. 4B.

To determine the impact of analyte flow on the temperature profile of the cantilever arms, IR images of the cantilever with and without the presence of isopropanol were recorded. In FIG. 4A, the cantilever (dashed line) is shown at 50 V bias without any analyte flow, the dark region at the tip is the hottest spot with a temperature of about 330° C. FIG. 4B shows the cantilever image with 2000 ppm molar concentration of isopropanol vapor under the same 50 V bias. FIG. 4C shows a line scan depicting average temperature variation along the arms of the cantilever. The inset shows the equivalent circuit based on the model resistors shown in FIG. 4A. As shown, the peak temperature at the tip was reduced by 30° C. in the presence of 2000 ppm of isopropanol vapor, while the temperature profile became wider. Interestingly, the side arms adjacent to the tip area exhibited an increase in temperature by about 20° C. The current in the sensor increased, i.e. the overall resistance decreased, in presence of isopropanol vapor. Thus, any exothermic reaction between the VOC and air could be ruled out in contrast with hot bead pellistors.

Figure 4D:
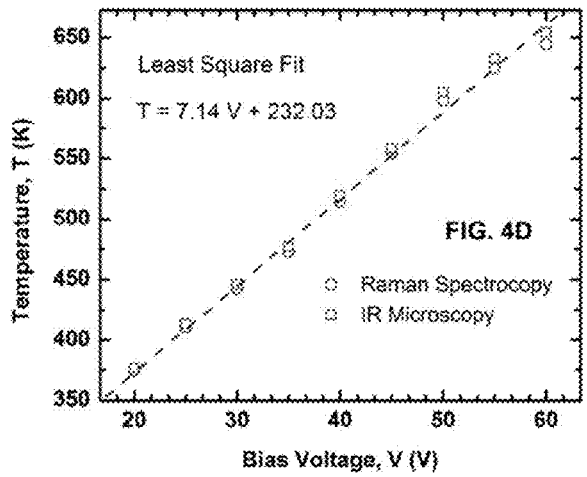
FIG. 4D presents the temperature calibration curve of the microcantilever of FIG. 2A with voltage bias using calibrated IR microscopy and Raman spectroscopy showing an identical linear trend for both.

FIG. 4D presents the change in the temperature at the tip with the bias voltage applied. The peak temperature at the tip was determined by IR microscopy and also from calibrated Raman spectroscopy. As shown, the peak temperature was found to vary from 105° C. to 330° C. as the applied voltage bias was increased from 20 to 50 V. The temperature was determined by calibrating the IR camera and the Raman peak shift using an identical cantilever on a temperature controlled hotplate. The voltage bias was swept from 0 to 50 V at 5 V intervals and the steady-state temperature was measured at each bias point. FIG. 4D shows only the 20-50 V bias range where the sensing experiments are done.

The experimentally determined temperature profiles for similar conditions as determined according to the models described previously are presented in FIG. 4C, and are also reproduced in FIG. 5A for comparison to theoretical models. FIG. 5B presents results obtained from the theoretical model described above. In FIG. 5B, the theoretically obtained electrical "path length" of the heated tip region (designated by $R_{tip}$ in FIG. 4A) is shown for different bias voltages at 2000 ppm of isopropanol vapor. In this context, electrical path length refers to the length of the hypothetical resistance $R_{tip}$ along the path of the current; which corresponds to the portion of the cantilever that undergoes a negative change in temperature in the presence of an analyte vapor. In order to calculate the electrical path length of $R_{tip}$ (denoted as $L_{tip}$), temperature profile at each bias point was calculated for no analyte vapor and for a given analyte vapor at a certain concentration. $L_{tip}$ strongly depends on the concentration and nature of the analyte. As shown in FIG. 5B, at less than a 14 V bias, $L_{tip}$ is not significant (uniform temperature distribution over most of the cantilever length), indicating negligible effects of analyte vapor on temperature distribution. However, above about 14 V bias, the value of $L_{tip}$ starts becoming significant in presence of isopropanol.

Although theoretically obtained $L_{tip}$ starts to increase after 14 V, the threshold voltage for isopropanol was experimentally observed to be about 18 V, which can be explained based on the postulate that an increase in $R_2$ offsets change in $R_{tip}$ (denoted by $R_2$ in FIG. 4C) below 18 V. Consequently, the total resistance ($R_{tip}+R_2$) remains unchanged below 18 V, keeping the current unchanged. After 20 V, $L_{tip}$ increases almost linearly with bias voltage, which indicates the extension of the $R_{tip}$ region along the side arms toward the base of the cantilever. Due to the tapered nature of the cantilever, this extension of the $R_{tip}$ region is expected to saturate as the wider edges of the region would not heat up at the same rate (with change in voltage) as the cantilever tip. This saturation state of $L_{tip}$ can be clearly seen in FIG. 5B above 40 V.

FIG. 6A shows the experimentally obtained normalized change in current caused by dilute vapor (2000 ppm concentration) of four different VOCs: isopropanol, methanol, hexane and acetone, as the applied voltage bias was varied from 15 to 50 V. Seven readings were averaged at each bias point and a 5-point moving average filtering was performed to ensure better consistency and noise reduction. From the measured data points, the approximate uncertainty in the threshold voltage was estimated to be ±0.05 V. As can be seen from FIG. 6A, each analyte exhibited a distinct threshold voltage ($V_{th}$) below which it does not cause any noticeable change in current. Although the current nearly saturated after about 20 V, tip temperature still increased with an increasing bias due to the higher power dissipation (I.e, self-heating), which is why further increase in the voltage bias can be carried out to observe additional sensor response despite having a fairly constant current through the device at that level.

The threshold voltage obtained for each analyte was observed to be very consistent over multiple sets of experiments performed in a period of more than six months utilizing several identical devices. To verify if a generic correlation indeed existed between $\Delta H_{vap}$ and $V_{th}$ as predicted by the model, threshold voltages of seven different analytes with latent heat varying over a wide range were determined. The plot of $V_{th}$ versus $\Delta H_{vap}$ is shown in FIG. 6C, where an excellent linear correlation was observed and $V_{th}$ was observed to vary only slightly with the change of concentration. This is in agreement with the model as discussed previously in which a correlation between $V_{th}$ and $\Delta H_{vap}$ was predicted, and clearly indicates that the well-defined correlation can be utilized to perform selective detection of VOC vapors from their unique threshold voltages.

The temperature of the by (measured using the IR camera) at the threshold voltage was found to be lower than the auto-ignition temperature for all the seven VOCs studied, ruling out any combustion related effects. Also, no effect of water vapor of similar molar concentration (2000 ppm) was observed (FIG. 3A) even up to a bias of 50 V, which is much higher than the expected $V_{th}$ of 23 V for water based on the $\Delta H_{vap}$ of 40 kJ/mol. This, therefore, rules out any interference from water vapor in realistic sensing environments.

In order to establish the utility of $V_{th}$ for uniquely identifying individual analytes, systematic measurements of device characteristics were performed as a function of analyte concentration. The results are shown in FIG. 7A and FIG. 7B for three different analytes—isopropanol, ethanol and toluene, which were chosen to cover a wide range of $\Delta H_{vap}$. As observed from FIG. 7A, the $V_{th}$ values corresponding to different analytes changed only slightly (0.6-0.75 V) when the concentration was reduced from 2000 ppm to 50 ppm.

The threshold current $I/I_0$ vs. the vapor concentration is shown in FIG. 7B for three different VOCs. The same is also done for the carrier gas dry UHP $N_2$ to obtain the background response for the carrier gas and the noise signal, which was found to be within 0.04% over the entire bias range (15-35 V). This limits the detectability of the threshold voltage as concentration goes down. Extrapolated curves indicate a noise limited resolution below 5 ppm with a sensor noise level of 0.04% change in output current. FIG. 7B also shows a linear relation between threshold current response with logarithm of concentration, which is common for many sensors.

Table 1, below shows the sensitivity of the sensor for 50 and 2000 ppm concentration of isopropanol, ethanol, toluene and acetone vapors. As shown, analytes exhibiting higher threshold voltage will have higher detection sensitivity, which is also evident in FIG. 7B, where the slope of the fitted line is higher for such an analyte. Table 1 also lists the rise and fall times of the sensor for different analytes. It can be observed that the rise/fall times are similar for all four analytes at high concentration (2000 ppm), however at low concentration (50 ppm) they start to deviate quite significantly (by up to 10 s). The rise/fall time decreases by several seconds as the voltage bias (i.e. cantilever temperature) goes up.

TABLE 1

| | $V_{th}$ | | | | Rise time | | | Fall time | | |
|---|---|---|---|---|---|---|---|---|---|---|
| Analyte | 2000 ppm | 1000 ppm | 50 ppm | Sensitivity % | 2000 ppm | 1000 ppm | 50 ppm | 2000 ppm | 1000 ppm | 50 ppm |
| Isopropanol | 18.0 | 18.2 | 18.7 | 0.172 | 15 | 21 | 54 | 22 | 30 | 78 |
| Ethanol | 23.0 | 23.2 | 23.75 | 0.224 | 14 | 21 | 51 | 19 | 27 | 72 |
| Toluene | 27.0 | 27.1 | 27.5 | 0.251 | 17 | 24 | 58 | 23 | 32 | 83 |
| Acetone | 29.0 | 29.1 | 29.6 | 0.256 | 14 | 22 | 53 | 20 | 27 | 75 |

To investigate any dependence of $V_{th}$ on analyte concentration, detection was performed with much diluted (down to ~50 ppm concentration) vapor of isopropanol, ethanol and toluene. The $V_{th}$ values were found to increase only by about 0.75 V as the vapor concentrations were reduced 40 fold from 2000 to 50 ppm (FIG. 7A). This indicates that $V_{th}$ remains effectively constant, and thus can be used to reliably identify VOCs over their significant detection range, especially for indoor environments.

Correlations between the magnitude of the molecular dipole moment of the analyte VOC and the magnitude of current change caused at a fixed applied bias were explored. FIG. 6D shows the percentage changes in current for seven VOCs (measured at a constant bias of 50 V) plotted against their dipole moments. It was found that as the dipole moment of the analyte increases, the response magnitude also increases, which is expected since the molecules with higher dipole moment are expected to have stronger interaction with the highly polar AlGaN surface.

The limit of detection (LOD) in terms of vapor concentration was also estimated from the simulation results corresponding to the threshold current response assumed to vary over the range of 0.001% and 0.1%. The results are presented in FIG. 8A for three different analytes. All of the responses can be seen to merge asymptotically at low concentration, which is supported by the experimental results as shown in FIG. 8B in which the extrapolated curves also intersect at low concentration. Such an intersection of extrapolated responses for various analytes is expected, as at very low concentration (i.e. below detection level), the various analyte vapors would produce very similar response to the carrier gas alone (i.e. $N_2$), which is basically defined by the system noise. The LOD for different analytes at 0.001% threshold current response as estimated from the theoretical models are tabulated in FIG. 8B.

The sensors used were studied over a period of at least a year, both in open air and in a closed chamber; and were subjected to higher applied biases (up to about 90 V) than those reported here. However, no noticeable change in device characteristics was observed in this time frame, which underscores high measurement reliability as well as thermal and chemical stability of the sensors.

Example 2

Figure 9A:
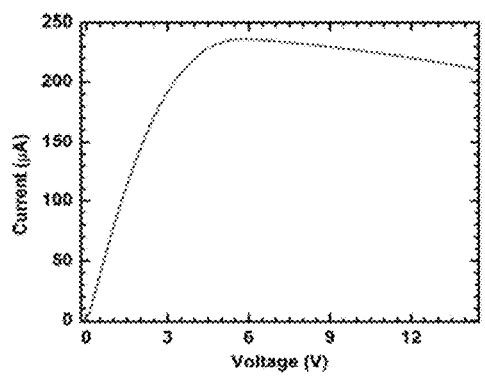
FIG. 9A presents the current/voltage (I/V) characteristics of a single channel microcantilever sensor.
Figure 9B:
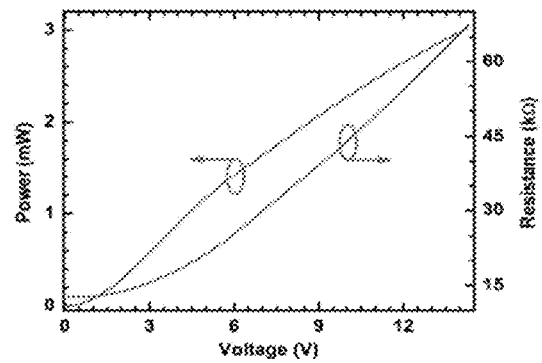
FIG. 9B illustrates the change in power and change in resistance of the sensor of FIG. 9A with change in bias voltage.

A single channel microcantilever was formed as described above with smaller dimensions (base width of about 18 μm, tip width of about 2 μm and thickness of about 0.7 μm). The conductivity of the AlGaN/GaN epilayer was also higher this time. FIG. 9A presents the I-V characteristics of the single channel microcantilever heater sensor and FIG. 9B illustrates the change of power and resistance with bias voltage for the microcantilever. The lower operating voltage and dissipated power can clearly be observed.

Figure 10A:
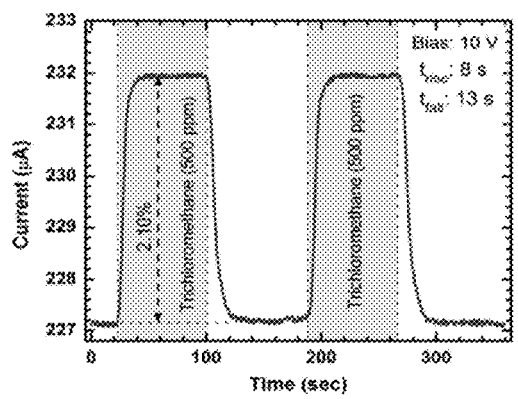
FIG. 10A illustrates the response of a sensor to 500 ppm trichloromethane in two consecutive cycles at 10 V DC bias.
Figure 10B:
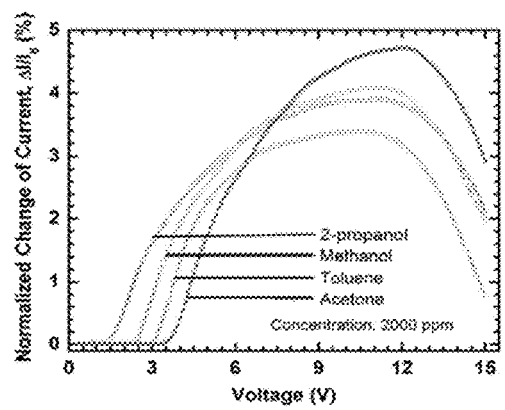
FIG. 10B presents normalized change in current (%) with change in bias voltage for a sensor response to 2-propanol, methanol, toluene and acetone at 2000 ppm molar concentration.

FIG. 10A presents the response of the device to 500 ppm of trichloromethane in two consecutive cycles at 10 V DC bias. In both exposure cycles, there was a change of about 2.1% in current. The rise time and fall time were 8 and 13 s respectively. Composite plots of normalized change in current (%) with change in voltage is shown in FIG. 10B for several different VOCs including 2-propanol, methanol, toluene and acetone at 2000 ppm molar concentration. As can be seen, there is a distinct voltage ($V_{th}$) for each analyte below which there is no detectable change in current.

Figure 10C:
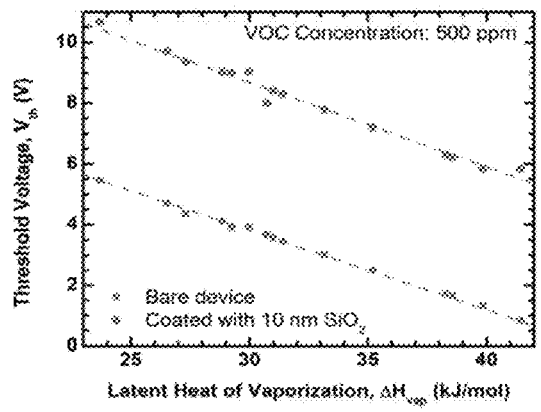
FIG. 10C illustrates the linear relationship between threshold voltage of sensing ($V_{th}$) and latent heat of evaporation ($\Delta H_{vap}$) for different VOCs at 500 ppm molar concentration for a bare microcantilever and a microcantilever coated with $SiO_2$.

A second single channel cantilever was formed that was identical to the first but included a 10 nm coating of silicon dioxide ($SiO_2$) on the surface. The linear relation between threshold voltage of sensing ($V_{th}$) and latent heat of evaporation ($\Delta H_{vap}$) for each of the different VOCs at 500 ppm molar concentration with each of the two sensors is shown in FIG. 10C. As can be seen, the device coated with $SiO_2$ exhibits an upward shift in $V_{th}$ by more than 4.5 V. This indicates an enhanced interaction of the analyte molecules with the cantilever tip when the AlGaN surface is bare, which is believed to lower the $V_{th}$.

Correlation between normalized change in current (%) at 10 V DC bias and dipole moment (μ) for VOCs at 100 and 500 ppm molar concentrations is shown for the uncoated cantilever in FIG. 11A. As can be seen, there was a linear relation for each analyte concentration. A similar reading for 2000 ppm molar concentration can be seen in FIG. 11B, taken from the same device shown in FIG. 11A and also for the cantilever coated with 10 nm $SiO_2$ but otherwise identical as referred to in FIG. 10C. For the oxide-coated device, there is no correlation between normalized change in current and molecular dipole moment, indicating a suppression of surface interaction promoted by the polar AlGaN surface that is only accessible on a bare device.

The normalized threshold response, defined by the normalized change in current within a 20 mV voltage range around $V_{th}$, is shown in FIG. 12A as a function of concentration for four analytes. As can be seen, the threshold response varies linearly with concentration, the asymptotes indicate a noise limited lower limit of detection below 1 ppm. The root mean square (rms) noise level of the entire detection scheme was determined to be 0.013% below 6 V, which is 3 times lower than the device mentioned in Example 1. FIG. 12B illustrates the shift of $V_{th}$ with concentration variation. At high concentration (>500 ppm) $V_{th}$ was found to be nearly constant, so that value was taken as the reference. At lower concentration (5 ppm), $V_{th}$ varies by about 140 mV. The shift in $V_{th}$ could be fitted reasonably well to a single exponential function, as shown in the figure.

The normalized change in current (%) obtained from the single channel microcantilever heater in presence of a combination of six analytes (100 ppm of each)—2-propanol, ethanol, methanol, toluene, acetone and hexane is shown in FIG. 13A. In FIG. 13B, the second derivative of the curve shown in FIG. 13A with respect to the applied bias (V) is illustrated. As can be seen, distinct peaks can be identified for each of the six analytes near their respective threshold voltages.

Example 3

A monolithic dual channel microcantilever heater as illustrated in FIG. 1D and FIG. 1E was formed. The cantilever had a base width of about 25 μm, tip width of about 4 μm, thickness of about 0.7 μm and was made of the same material as mentioned in Example 2. The heater and sensor channels, as indicated by 40 and 30 respectively in FIG. 1E, were separated by a narrow region 35 with <1 μm width, realized by removing AlGaN from that region.

The system was utilized with the sensor channel biased at a fixed 100 mV DC bias and in the secondary heating mode, the current of the sensor channel was measured while the heater channel bias was swept. In the self-heating mode, the heater channel acted alone under the variable bias voltage.

The linear relationship between threshold voltage of sensing ($V_{th}$) and latent heat of evaporation ($\Delta H_{vap}$) for each channel the cantilever is illustrated in FIG. 14 for different VOCs at 100 ppm molar concentration. As can be seen, the curve for the secondary heating mode along the sensing channel measured using the sensor channel is steeper, with a 120% increase in threshold voltage sensitivity, than the curve for the self-heating mode using the heater channel. The self-heating mode undergoes an increased electric field around the tip as the bias goes up; which is likely to enhance the molecular interaction at a lower bias, hence reducing the slope of the curve.

Example 4

A split tip dual channel micro cantilever sensor as illustrated in FIG. 1F was formed. The cantilever had a base width of about 25 μm, tip width of about 2 μm for each channel, thickness of about 0.7 μm and was made of the same material as mentioned in Examples 2 and 3. The heater and sensor channels, as indicated by 41 and 31 respectively in FIG. 1G, were separated by a narrow air gap.

The normalized change in resistance (%) for 100, 500 and 1000 ppm of 2-propanol, as measured using in secondary heating mode of the sensor is shown in FIG. 15A. The sensor channel was biased at fixed 100 mV DC. As 2-propanol has a lower heat conductivity than pure dry $N_2$, the response was negative. At higher concentration, the effect was more pronounced.

FIG. 15B presents the first derivative of each response curve shown in FIG. 15A, with respect to V. Each curve shows two peaks for the same analyte, the first one (within 1.2-1.4 V) is for the onset of the sensing behavior on the heater arm, marked by a sudden change of heating. The second peak, at much higher bias, is due to the sensing effects exhibited by the sensor arm. This peak is strongly correlated with concentration.

FIG. 16A illustrates the first derivative of normalized change in resistance (%) for 100 ppm (each) of a mixture of ethanol and methanol, and FIG. 16B presents the same information for a mixture of 1-propanol and 2-propanol for the split tip dual channel microcantilever sensor. As can be seen, each analyte has a low voltage peak corresponding to self-heating sensing and a high voltage peak indicative of secondary heating induced sensing.

It will be appreciated that the foregoing examples, given for purposes of illustration, are not to be construed as limiting the scope of this disclosure. Although only a few exemplary embodiments of the disclosed subject matter have been described in detail above, those skilled in the art will readily appreciate that many modifications are possible in the exemplary embodiments without materially departing from the novel teachings and advantages of this disclosure. Accordingly, all such modifications are intended to be included within the scope of this disclosure. Further, it is recognized that many embodiments may be conceived that do not achieve all of the advantages of some embodiments, yet the absence of a particular advantage shall not be construed to necessarily mean that such an embodiment is outside the scope of the present disclosure.

What is claimed is:

1. A system for identifying a volatile organic compound; the system comprising:
    a fluid flow path configured for carrying a volatile organic compound;
    a power source configured for supplying a driving voltage; and
    a triangular microcantilever held in electrical communication with the power source, the microcantilever comprising a first arm extending from a base, a second arm extending from the base, and a tip at a junction of the first arm and the second arm, the first arm having a cross section that decreases in size with a first regular taper, the first regular taper beginning at the base and extending to the tip, the second arm having a cross section that decreases in size with a second regular taper, the second regular taper beginning at the base and extending to the tip, the tip being in the fluid flow path, wherein upon contact between the microcantilever and the volatile organic compound in conjunction with application of the driving voltage to the microcantilever, the first arm exhibits a first electrical resistance, the second arm exhibits a second electrical resistance, and the tip exhibits a third electrical resistance, the third electrical resistance differing from the first and second electrical resistances.

2. The system of claim 1, wherein the power source is configured for supplying a variable voltage bias to the microcantilever.

3. The system of claim 1, wherein the tip comprises a material of formation that differs from a material of formation of the first arm and from a material of formation of the second arm.

4. The system of claim 1, wherein the microcantilever defines multiple channels, each channel being in independent electrical communication with the power source, each channel defining a length along the microcantilever, each of the multiple channels being separated from one another along their respective lengths.

5. The system of claim 4, the multiple channels including at least two channels that are separated from one another by an air gap along at least a portion of their respective lengths.

6. The system of claim 1, the microcantilever comprising a polar semiconductor.

7. The system of claim 1, the microcantilever comprising a wide bandgap semiconductor.

8. The system of claim 7, the microcantilever comprising a Group III-V, Group II-V, or Group II-VI wide bandgap semiconductor.

9. The system of claim 1, the microcantilever comprising multiple semiconductors in a stacked arrangement.

10. The system of claim 9, the microcantilever comprising a Group III-V heterojunction composite material.

11. The system of claim 10, the microcantilever comprising an AlGaN/GaN heterojunction composite material.

12. A method for detecting a volatile organic compound comprising:
    contacting a vapor containing a volatile organic compound with a triangular microcantilever, molecules of the volatile organic compound in the vapor condensing in close proximity of the microcantilever upon the contact, the microcantilever comprising a first arm extending from a base, a second arm extending from the base, and a tip at a junction of the first arm and the second arm;
    applying a voltage across the microcantilever and thereby heating the microcantilever, wherein under the applied voltage the first arm exhibits a first electrical resistance, the second arm exhibits a second electrical resistance, and the tip exhibits a third electrical resistance, the third electrical resistance differing from the first and second electrical resistances, the heating of the microcantilever causing the condensate of the volatile organic compound to vaporize and vary the third electrical resistance;
    monitoring one or more electrical characteristics of the microcantilever to determine a threshold voltage at which the one or more electrical characteristics exhibits a detectable change, the threshold voltage being indicative of the volatile organic compound.

13. The method of claim 12, wherein the voltage comprises a variable DC voltage bias.

14. The method of claim 13, wherein the one or more electrical characteristics comprises the change in current through the microcantilever as the voltage bias is varied.

15. The method of claim 14, wherein the threshold voltage is a mid-value voltage of a lowest 0.1 volt range within which the current magnitude through the microcantilever varies by 0.05% or more.

16. The method of claim 12, wherein the one or more electrical characteristics comprises a magnitude of current upon contact of the microcantilever with the volatile organic compound.

17. The method of claim 12, the microcantilever comprising multiple channels that extend along a length of the microcantilever, each of the multiple channels being separated from one another along their respective lengths, the method further comprising independently applying voltage to each of the multiple channels.

18. The method of claim 17, wherein the voltage applied to at least one of the multiple channels comprises a fixed voltage bias and the voltage applied to at least one other of the multiple channels comprises a variable voltage bias.

19. The method of claim 18, wherein the one or more electrical characteristics are monitored for a channel to which a fixed voltage bias has been applied.

20. The method of claim 12, wherein the one or more electrical characteristics comprises the threshold current response and/or the normalized change in resistance as the voltage applied to the microcantilever is varied.

21. The method of claim 20, wherein the fluid contains multiple volatile organic compounds.

22. The method of claim 21, the method further comprising determining a second derivative of the threshold current response.

23. The method of claim 21, the method further comprising determining a first derivative of the normalized change in resistance.

\* \* \* \* \*